(12) United States Patent
Johnson et al.

(10) Patent No.: US 6,361,508 B1
(45) Date of Patent: Mar. 26, 2002

(54) PERSONAL EVENT MONITOR WITH LINEAR OMNIDIRECTIONAL RESPONSE

(75) Inventors: Mark A. Johnson, Rensselaer; Paul J. Cote, Clifton Park, both of NY (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 09/553,177

(22) Filed: Apr. 20, 2000

(51) Int. Cl.[7] .......................... A61B 5/103; A61B 5/117
(52) U.S. Cl. ..................................................... 600/595
(58) Field of Search .............................. 600/595, 500, 600/504, 547, 552, 510, 553, 587; 128/782; 340/573; 702/150

(56) References Cited

U.S. PATENT DOCUMENTS

| | | | | |
|---|---|---|---|---|
| 5,146,206 A | * | 9/1992 | Callaway | 340/573 |
| 5,197,489 A | * | 3/1993 | Conlan | 128/782 |
| 5,879,309 A | * | 3/1999 | Johnson et al. | 600/552 |
| 5,913,826 A | * | 6/1999 | Blank | 600/500 |
| 5,966,680 A | * | 10/1999 | Butnaru | 702/150 |

* cited by examiner

*Primary Examiner*—Kevin Shaver
*Assistant Examiner*—Brian Szmal
(74) *Attorney, Agent, or Firm*—John F. Moran; Michael C. Sachs

(57) ABSTRACT

A monitor device for monitoring the activity of an individual to provide an alarm for anomalous by the individual. The device includes a triaxial accelerometer adapted to measure simultaneously measure acceleration in three orthogonal, linear axes and generate a voltage output identifying the amplitude and frequency of detected motion by the individual in each axis. Also included is interface electronics for receiving the voltage outputs and buffering the voltage outputs to generate a first reference voltage for each axis of the accelerometer. Amplifier electronics amplifies each voltage output and compares each voltage output to the first reference voltage to produce a digital signal. A microcontroller receives the digital signal to compare it to an adjustable second reference voltage. The microcontroller is programmed to discriminate between normal activity and anomalous activity by identifying sensor activity within sequences of preselected time intervals and sending an alarm signal upon detection of the anomalous activity. An alarm for receiving the alarm signal and signaling an alarm completes the device.

9 Claims, 2 Drawing Sheets ic physical activity. More particularly the invention relates to a monitor responsive to anomalous activity while distinguishing the same from casual activity associated with normal quiet daytime activities.

PERSONAL EVENT MONITOR WITH LINEAR OMNIDIRECTIONAL RESPONSE

The invention described herein may be manufactured, used, and licensed by or for the U.S. Government for government purposes.

FIELD OF THE INVENTION

The present invention relates to a monitor for alerting those responsible for the care of individuals to the onset of anomalous physical activity. More particularly the invention relates to a monitor responsive to anomalous activity while distinguishing the same from casual activity associated with normal quiet daytime activities.

BACKGROUND OF THE INVENTION

The problem of alerting caregivers to the onset of distress or to a medical disorder such as a seizure has always existed. The specific problem is to alert those responsible for the care of individuals to the onset of anomalous physical activity and to distinguish this type of activity from normal casual motion. The anomalous physical activity ranges from that associated from distress while sleeping to that associated with certain medical disorders such as epilepsy. The individual may suffer from a condition where prompt detection and enhanced accuracy in documentation of medical episodes is required to assist in improving care. The device would have great benefit for parents, teachers and other caregivers who cannot continuously and visually monitor the individual in their care. It would be a great benefit of having a monitor useful in the home or in group environments such as a classroom of students with special needs.

Caregivers of individuals afflicted with certain illnesses or conditions such as epilepsy are required to closely and continuously monitor those under their care. This is also the case for parents concerned with restless activity in their children during sleeping hours. U.S. Pat. Nos. 5,523,742, 5,610,590, and 5,879,309 describe monitors developed to address these problems.

Continuous visual monitoring of individuals is usually impossible and periodic monitoring is often insufficient. The monitors described in U.S. Pat. Nos. 5,523,742 and 5,610, 590 provide relief during sleeping hours, but are inappropriate for reliably discriminating seizures from the casual activity associated with normal quiet daytime activities. The use of either of these monitors would produce an unacceptably high false alarm rate resulting in undue anxiety and, perhaps, even a loss of faith in the device. The monitor described in U.S. Pat. No. 5,879,309 employs a custom made sensor that is not 5 commercially available and is costly to produce. The sensor used in U.S. Pat. No. 5,879, 309 also has a highly nonlinear response that does not allow optimal adjustments of monitor sensitivity. It also lacks the sensitivity to respond to low amplitude motion that is characteristic of certain types of disorders.

Accordingly, one object of the present invention is to provide a sensor that is sensitive to respond to low amplitude motion.

Another object of this invention is to provide a monitor device that minimizes false alarms due to reading, walking or related casual activities.

A specific object of this invention is to provide a monitor device that uses a new, commercially available sensor having a linear, omnidirectional response with high sensitivity, ultra-low power consumption, low cost, and small size.

Other objects will appear hereinafter.

SUMMARY OF THE INVENTION

It has now been discovered that the above and other objects of the present invention may be accomplished in the following manner.

Specifically, the present invention comprises a monitor device for monitoring the activity of an individual to provide an alarm for anomalous by the individual. The device incorporates a new, commercially available sensor having desired features of linear, omnidirectional response, high sensitivity, ultra-low power consumption, low cost and small size.

Also included in the monitor device of the present invention is interface electronics for receiving the voltage outputs and buffering the voltage outputs to generate a first reference voltage for each axis of the accelerometer. Each voltage output is amplified and compared to a first reference voltage to produce a digital signal.

A microcontroller compares the digital signal to an adjustable second reference voltage. The microcontroller discriminates between normal activity and anomalous activity by identifying sensor activity within sequences of preselected time intervals and sending an alarm signal upon detection of the anomalous activity. An alarm for receiving the alarm signal and signaling an alarm completes the device.

BRIEF DESCRIPTION OF THE DRAWINGS

For a more complete understanding of the invention, reference is hereby made to the drawings, in which.

DETAILED DESCRIPTION OF THE PREFERRED EMBODIMENT

The present invention has many advantages. It provides a means for alerting caregivers to anomalous physical activity while minimizing false alarms due to reading, walking, or related casual activities. The monitor described in detail below is small, lightweight, portable, simple to use, and inexpensive to produce.

Figure 1:
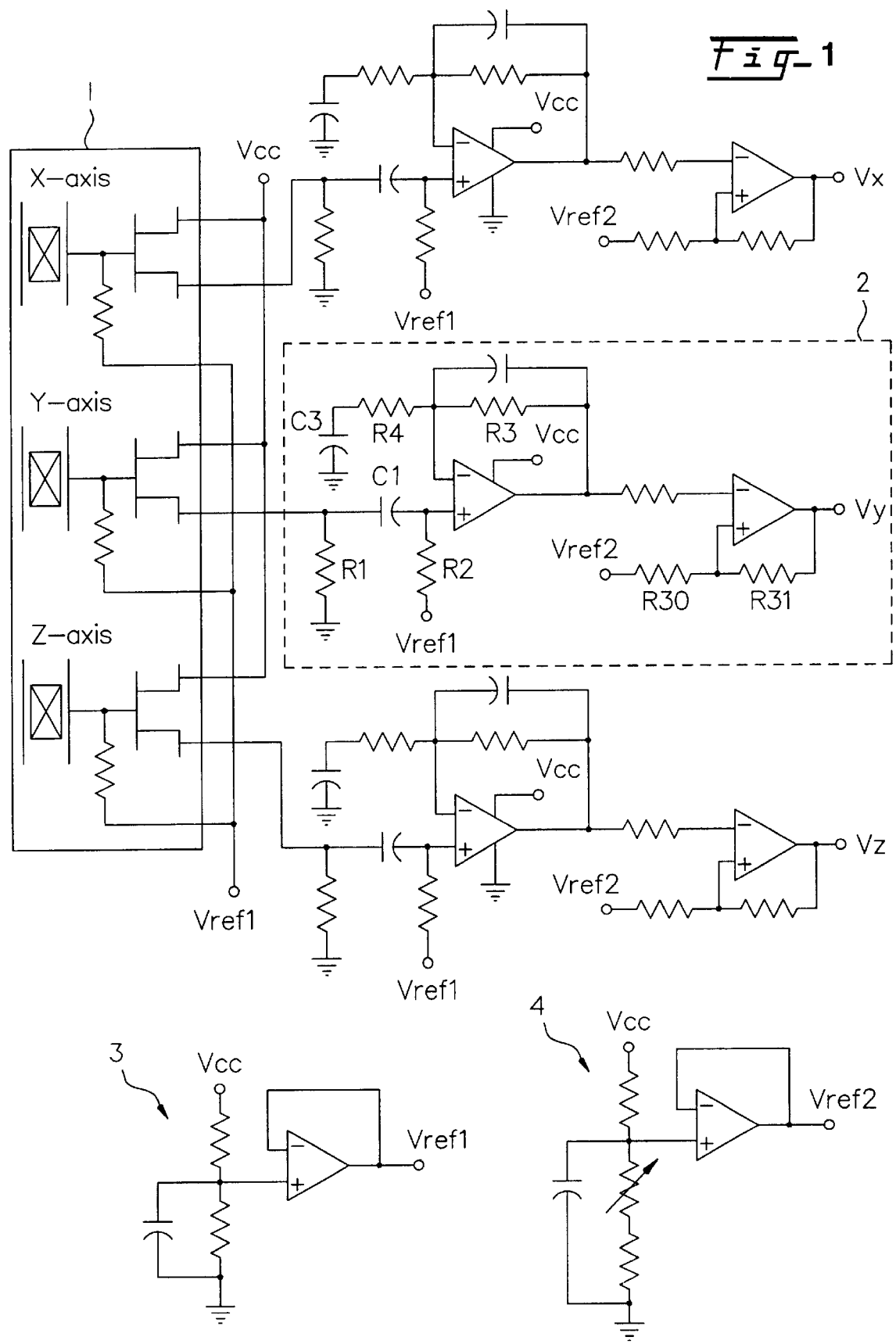
FIG. 1 is a circuit diagram illustrating the monitor electronics connected to the sensor.

Two separate monitors have been developed under the present invention. One is for daytime use and one for use during the night. The monitors are conceptually identical, differing only in the type of alarm and power supply used. Shown in FIG. 1 is the electronics used in the daytime monitor. The monitor device employs a small, inexpensive, low-power, triaxial accelerometer, 1, which is also designated U3 in FIG. 1. Accelerometer 1 is used to detect anomalous physical activity in an individual, where the anomalous activity may, for example, be associated with a seizure episode. Accelerometer 1 simultaneously measures acceleration in three orthogonal axes, labeled x, y and z. Upon activation by physical motion, the accelerometer 1 generates a voltage output V that provides a measure of the amplitude and frequency of the motion. A preferred accelerometer for use in the present invention is known as Accelerometer ACH-04-08-05, manufactured by Measurement Specialties Incorporated, located in Norristown, Penn.

The ACH-04-08-05 operates over a temperature range of from −40° C. to 85° C., much larger than the normal environment for humans, and nominal sensitivity will typically changes less than 2 dB over that range of temperature.

The accelerometer outputs are buffered by internal JFET's which require external biasing. The interface electronics, shown in dashed oval 2, are identical for all three axes, so only the y-axis electronics will be described. The JFETs are biased using a source-resistor bias in a source-follower configuration. $V_{ref1}$ is generated using a buffered voltage divider, shown in FIG. 1 as 3 generally, and is set to 1.64 VDC using a 3 VDC supply. A 0.6 DC voltage drop across the JFET gate results in approximately 2.24 volts at the JFET's source. The 2.24 volts across R1 to ground biases the JFET using 2.24 μA of current. Therefore, 7.72 μA are required to bias all three axes of accelerometer 1. C1 blocks the DC bias offset and the R2 forms a high pass filter with a pole at 0.16 Hz. R3 and R4 define the system gain of 294. R4 and C3 form another high pass filter with a pole at 2.12 Hz and minimize DC offset at the output by setting the DC gain at 1.

The amplified signal is then compared with a reference voltage $V_{ref2}$ that is set by a user adjustable buffered divider shown in FIG. 1 generally as 4. R30 and R31 provide 30 mv of hysteresis. The output of the comparator circuit is a digital signal that is analyzed by the microprocessor, shown generally as 5 and also as U4 in FIG. 2. The microcontroller discriminates normal casual activity from anomalous activity by identifying sensor activity or lack of activity within sequences of preselected time intervals. The hex rotary switch 6 in FIG. 2 sets the time interval and total sampling time used by microprocessor 5. Switch settings are given below in Table I.

TABLE I

SWITCH SETTINGS

| value | frequency (hz) | time (sec.) | alarm (seconds) |
|---|---|---|---|
| 0 | f > 1.0 | 5 | 60 |
| 1 | f > 1.0 | 10 | 60 |
| 2 | f > 1.3 | 5 | 60 |
| 3 | f > 1.3 | 10 | 60 |
| 4 | f > 2.0 | 5 | 60 |
| 5 | f > 2.0 | 10 | 60 |
| 6 | f > 4.0 | 5 | 60 |
| 7 | f > 4.0 | 10 | 60 |
| 8 | f > 1.0 | 5 | continuous |
| 9 | f > 1.0 | 10 | continuous |
| A | f > 1.3 | 5 | continuous |
| B | f > 1.3 | 10 | continuous |
| C | f > 2.0 | 5 | continuous |
| D | f > 2.0 | 10 | continuous |
| E | f > 4.0 | 5 | continuous |
| F | f > 1.0 | 10 | continuous |

The values of $V_{ref2}$ sets the sensitivity of the monitor device of this invention. This combination of user selectable parameters permit an unlimited range of settings to accommodate a wide variety of conditions. If the microprocessor 5 detects anomalous activity or if the battery monitor, shown as 7 in FIG. 2, signals a low-battery condition, an alarm is activated. The listing of the microcode for microprocessor 5 of the monitor device are given below in Table II. This code is the microcode listing for the microprocessor used in the daytime implementation, using Microchip PIIC16LC585.

TABLE II

CODE LISTING

```
; bcf STATUS,5=> selects Special Function Registers in Bank 0
    (PORTA, PORTB)
; bsf STATUS,5 => selects Special Function Registers in Bank 1
    (TRISA, TRISB, OPTION)
; general purpose registers are in 20h->7Fh in Bank O & AOh-> in
    Bank 1
; minimize power:
    1 ) all unused 1/O ports set to outputs
    2.) tie MCLR (bar) to Vdd
    3.) don't use portb pull-ups
    4.) TMRO to Vdd or Vss
    5.) don't use power-up timer (requires RC timer)
; individual flag bits are set regardless of the status of their
    corresponding mask bit
; or the GIE bit
;
RADIX DEC
PROCESSOR PIC16C558
#include<P16c558.inc>
EVENT1      equ 20h
EVENT2      equ 21h
TEMP        equ 22h
WIN         equ 23h
CFG         equ 24h
CFG_IN      equ 25h
BEEP1       equ 26h
BEEP2       equ 27h
BEEP_ON     equ 28h
BEEP_OFF    equ 29h
COUNT       equ 2ah
COUNTX      equ 2bh
DBG         equ 2ch
MASK        equ b'00011111'
; Board design should be much simpler using RBO–RB3 for inputs and
    RB4–RB7 for interrupts.
; Could use INTO for the battery monitor, but cannot invision any
    problems if I don't.
; If a window is missed, the routine will check the status of the
    battery anyway.
; If it is the battery monitor that wakes up the processor, and there is
    no other motion;
(axis-interrupts) then the battery status will be checked anyway upon
    return to start.
;If the battery monitor inturrupts during the window tests and port
    interrupt changes are
; disabled it will be tested upon return to start or an alarm will sound
    anyway if no
; windows are missed.
;
;    RA0 = output buzzer
;    RA1 = output buzzer
;    RA2 = output buzzer
;    RA3 = output buzzer
;    RA4 = output buzzer
;
;    RBO = input window parameter
;    RB1 = input window parameter
;    RB2 = input window parameter
;    RB3 = input window parameter
;    RB4 = input battery monitor
;    RB5 = input x-axis (hight = 0.36 Vdd)
;    RB6 = input y-axis
;    RB7 = input z-axis
;
Vss = ground = Vpp;
Vdd – 3.0 Vdc
;
;    RB3, RB2, BR1, BR0 = config input:
;    3210    m(ms)    time(s)    (# windows)    timer enable
;
;0  0000    1000     5          5              1
;1  0001    1000     10         10             1
;2  0010    750      5          7              1
;3  0011    750      10         13             1
;4  0100    500      5          10             1
;5  0101    500      10         20             1
;6  0110    250      5          20             1
```

TABLE II-continued

CODE LISTING

```
;7      0111    250    10     40     1
;8      1000    1000   5      5      0
;9      1001    1000   10     10     0
;A      1010    750    5      7      0
;B      1011    750    10     13     0
;C      1100    500    5      10     0
;D      1101    500    10     20     0
;E      1110    250    5      20     0
;F      1111    250    10     40     0
origin  org h'0000;           start program here
        go to       start
        go to       start       ;location 0001
        go to       start       ;location 0002
        go to       start       ;location 0003
;       interrupt service routine (0004)
        btfsc INTCON,2    ;timer overflow?
        goto int_a
;       If not timer, then battery or one of sensor axis
;       Mask RB interrupts. Yes, CIE is now cleared and disables all
        further interrupts, but
;       don't permit interrupts when exciting the interrupt service
        routine either. Don't
;       want battery alarm to be affected by interrupts. More
        importantly, only permit one
;       axis interrupt at a time in a window. Otherwise __nms will be
        extended as it keeps
;       getting interrupted!
        bcf INTCON,3      ;Mask further RB port change interrupts
        bcf INTCON,0
        bsf EVENT1,0      ;axis change (although a possible low
                           battery interrupt)
retfie                    ;will finish, even if GIE = 1 since RB
                           interrupts masked
int_a bcf INTCON,2        ;clear TMRO interrupt
      bsf EVENT2,0        ;TMRO event
      retfie              ;GIE set; enable all unmasked interrupts
start call init           ;initialize registers & read window
                           definitions
;       wait 2 seconds for buzzer to stabilize, should also be enough
        time for MAX809
;       to assert. (typically 140 ms). If MAX 809 is not ready-> low
        battery. MAX809
;       keeps asserting reset (low) if battery voltage remains low
        call __2s
        call —2s           ; wait for circuit to stabilize
        call MAX809        ; check battery voltage
        call beep—2        ; to indicate everything is O.K.
starta call init           : call init and MAX809 twice on startup - who
                            cares?
        call MAX809
        bftss PORTA,4      ; no debug mode, PCB layout was too complex!
;       call debug
        movfw PORTB ; clear PORTB mismatch & enable interrupt
        movlw b'1000100'   ;execute code inline on PRFB interrupt
        movwf INTCON
        sleep              ; sleep until sensor change
        movfw COUNT
        movwf COUNTx
acquire decfsz  COUNTx    ; will go here upon wake-up
        goto loop
        goto alarm
loop clrf EVENT1           ; EVENT1 set if any axis input exceeds
                            threshold
        call __WINms       ; wait window width for EVENT! to set
        btfsc EVENT1,0     ; port change during delay?
        goto acquire       ; port change occurred during delay
        goto starta
alarm clrf INTCON          ; forces manual reset alarm mode
        btfsc PORTB,2      : bit 2 = 1 disables auto-shut down mode
        goto alarm1
        movlw 30           : approximately 30 second alarm
        movwf COUNTx       ; COUNTx is temporary anyway
alarma call beep__1
        decfsz COUNTx
        goto alarma
        goto starta        ; start over again
alarm1 call beep__1        ; seizure, no limit on alarm
        goto alarm1
init clrf INTCON           ; don't allow interrupts at first
        clrf STATUS        ; clear upper three bits (see book)
        bsf STATUS,5       ; set RPO to use bank 1 for TRISA, TRISB,
                            and OPTION
        movlw b'00000000'  ; POPTA1/0; Output= 0 Input=1
        movwf TRISA
        movlw b'11111111'  ; PORTB1/0; Output= 0 Input=1
        movwf TRISB
        clrwdt             ; book says do it!
        bsf STATUS,0
:       assign prescalar 256 to TMRO and ensure portB pull-ups are
        disabled
        movlw b'11000111'
        movfw OPTION_REG
        bcf     STATUS,0   ; book says do it!
        bcf     STATUS,5   ; clear RPO to back to bank 0
        clrf    PORTA      ; all outputs low
        call    config     ; window definition
        clrf    EVENT1
        clrf    EVENT2
        return
MAX809  btfsc PORTB,4     ; MAX809 = => low battery
        return
MAX809a call beep__2
        goto MAX809a       ; MAX809 not set
        return
__2s  movwf  TEMP          ; 2-second delay
; Don't allow port interrupts in this routine
        clrf INTCON
        clrf EVENT2
        movlw 192
        movwf TMRO
        movlw b'10100000'
        movwf INTCON
__2sa btfss EVENT2,0
        goto __2sa
        CLRF INTCON
        movfw TEMP
        return
__500ms movwf TEMP         ; 500 ms delay
; Don't allow port interrupts in this routine
        clrf INTCON
        movlw 240
        clrf EVENT2
        movwf TMRO
        movlW b'10100000'
        movwf INTCON
__500msa btfss EVENT2,0
        goto __500msa
        CLRF INTCON
        movfw TEMP
        return
__30ms movwf TEMP          ; 30 ms delay
Don't allow port interrupts in this routine
        clrf INTCON
        clrf EVENT2
        movlw 255
        movwf TMRO
        movlw b'10100000'
        movwf INTCON
__30msa btfss EVENT2,0
        goto __30msa
        clrf INTCON
        movfw TEMP
        return
-WINms     movwf TEMP    ; WINDOW delay
Must allow port interrupts in this routine
        clrf INTCON
        clrf EVENT2
        movlw 255
        movlw WIN
        movwf TMRO
; allow 1 event on axis; RB port disabled in interrupt service routine
; GIE bit reset in interrupt service routine
        movfw PORTB       ; needed to clear mismatch condition! -
                           558 requires this
```

TABLE II-continued

CODE LISTING

```
        movlw    b'10101000'
        movwf    INTCON
_WINmsa btfss    EVENT2,0
        goto     _WINmsa
        clrf     INTCON        ; no interrupts allowed upon exit
        movfw    TEMP
        return
beep_2  movwf    BEEP2
        call     beep_off
        call     _500ms
        call     beep_40
        call     beep_off
        call     _30ms
        call     _30ms
        call     _30ms
        call     _30ms
        call     beep_40
        call     beep_off
        call     _500ms
        movfw    BEEP2
        return
beep_off movwf   BEEP_OFF
        CLRW     PORTA
        MOVFW    BEEP_OFF
        return
debug   movfvv   COUNT         ; remains in debug mode until
                               powered off/on
        movfw    COUNTX
        bcf      PORTA,2
        call     _500MS        ; first zero volts for 400ms
        bsf      PORTA,2
        call     _30ms         ; show 3lms pulse
        bsf      PORTA,2
        call     _500ms        ; wait another 400ms
        bsf      PORTA,2
        call     _WINms        ; show window width
        bsf      PORTA,2
        call     _500ms        'wait another 400ms
        bsf      PORTA,2
debug_a decfsz   COUNTX        ; show entire time (window*count)
        goto     debug_b
        goto     debug_c
debug_b call     _WINms
        goto     debug_a
debug_c bcf      PORTA,2
        call     _500ms
debug_  movfw    PORTA         ; just keep showing sensor input
        movwf    DBG           ; I don know why you can't just
        rrf      DBG,w         ; rrf the w register, but you can't
        andlw    b'01000000'
        movwf    PORTA
        goto     debug_d
config  movwf    CFG
        movfw    PORTB         ; latch switch settings
        clrf     CFG_IN        ; swap bits 2&3 and 0&1
                               because of circuit
        btfsc    PORTB,3
        bsf      CFG_IN,2
        btfsc    PORTB,2
        bsf      CFG_IN,3
        btfsc    PORTB,1
        bsf      CFG_IN,0
        btfsc    PORTB,0
        bsf      CFG_IN, 1
        movfw    CFG_IN
        andlw    b'00001111'
        addwf    PCL           ; offset PCL by the amount in w
        goto     zzero         ; the defaults
        goto     one
        goto     two
        goto     three
        goto     four
        goto     five
        goto     six
        goto     seven
        goto     zzero
        goto     one
        goto     two
        goto     three
        goto     four
        goto     five
        goto     six
; All counts incremented by 1 because of decfz test in main loop
seven   movlw    41
        movwf    COUNT
        movlw    248
        movwf    WIN
        return
six     movlw    21
        movwf    COUNT
        movlw    248
        movwf    WIN
        return
five    movlw    21
        movwf    COUNT
        movlw    240
        movwf    WIN
        return
four    movlw    11
        movwf    COUNT
        movlw    240
        movwf    WIN
        return
three   movlw    14
        movwf    COUNT
        movlw    232
        movwf    WIN
        return
two     movlw    8
        movwf    COUNT
        movlw    232
        movwf    WIN
        return
one     movlw    11
        movwf    COUNT
        movlw    224
        movwf    WIN
        return
zzero   movlw    6             ; 5 - 1 second windows
        movwf    COUNT
        movlw    224
        movwf    WIN
        return
beep_40 movwf    BEEP_ON
        clrw
        xorlw    MASK
        movwf    PORTA
; repeat previous 2 instructions to obtain 40ms at 32.768 kHz
        movfwBEEP_ON
        return
        goto
start
; repeat previous instruction to fill remaining memory space
END
```

Figure 2:
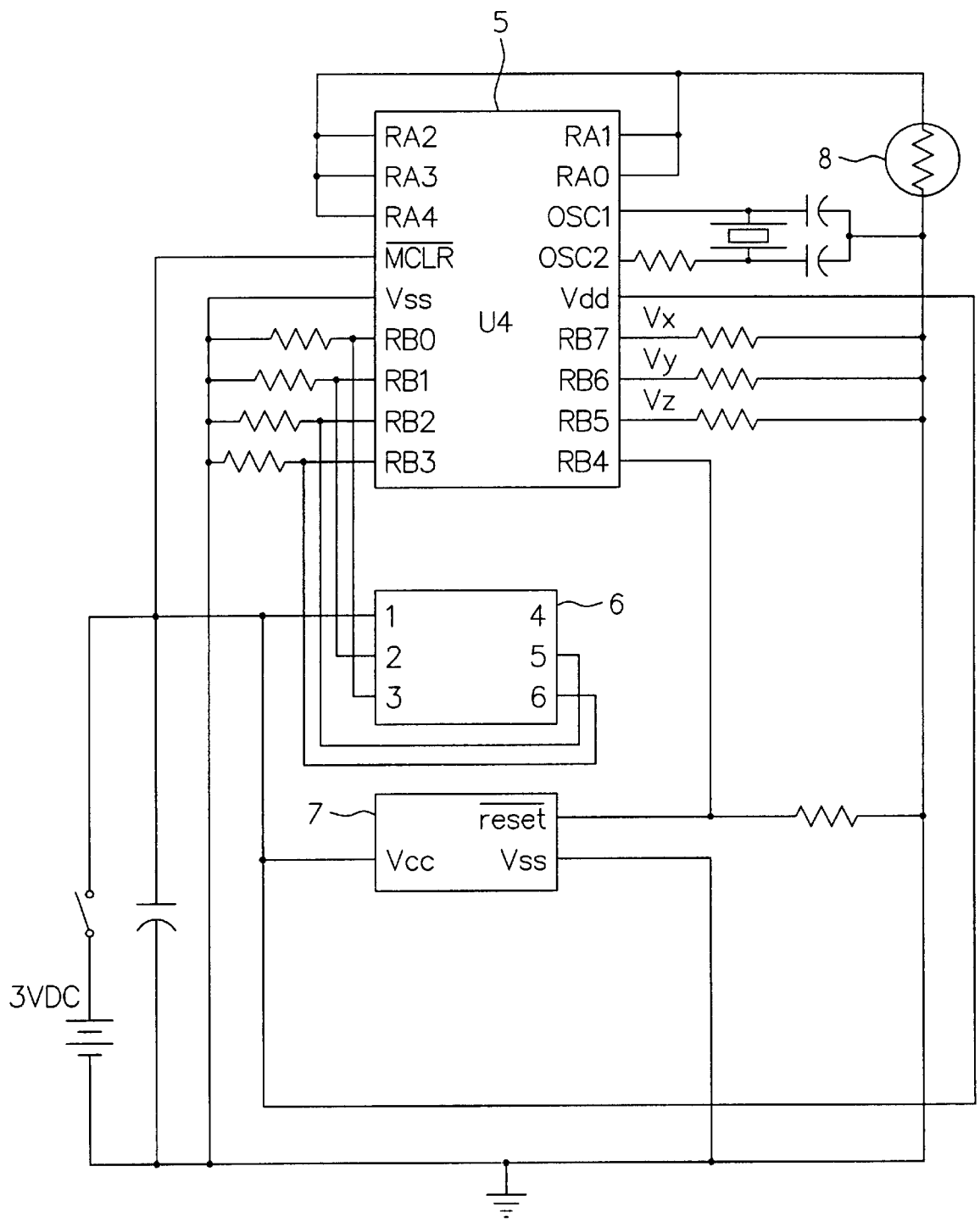
FIG. 2 is a circuit diagram of the electronics in conjunction with the microprocessor and alarm.

The alarm for the daytime monitor is an acoustic transducer 8 in FIG. 2. The audible signal for anomalous physical activity is distinct from that for a low battery condition. If unusual activity is detected, switch 6 setting, shown in FIG. 2, determines whether the alarm is active until the monitor is manually reset, or if it automatically resets after a preselected period of time. Power for the daytime monitor is derived from a standard coin cell battery, shown in FIG. 2 as 3VDC. Battery life is difficult to estimate since the oscillator circuitry of the processor is disabled to conserve power until activity is detected. Battery life is also a function of the number of alarms. A battery life of approximately 2700 hours is expected using a Panasonic® 2032 coin cell lithium battery.

The nighttime monitor transmits a FCC compliant radio frequency signal to a remote, compatible receiver when the alarm criteria are satisfied. The receiver then activates the desired alarm mechanism, such as a radio, lamp or buzzer. The signal is retransmitted periodically until the monitor is manually reset. In addition to the remote alarm, a LED on the monitor continuously flashes at a rate that indicates if the alarm is the result of a potential seizure or low battery.

Power for the nighttime monitor is derived from a standard miniature 12 volt battery. A Maxim MAX874 low-dropout precision voltage reference is utilized to supply 4 volts to the monitor circuitry.

The daytime monitor is small and easily attached to an individual. The power switch is preferably recessed on the side of the monitor and is the only means of resetting the monitor. There are internal adjustments that are available to permit optimization of the monitor response for each application. In an effort to conserve battery life, no indicator is used in the daytime mode to notify the user that the device is operational. Instead, the monitor beeps twice in the daytime mode or the LED flashes twice for the nighttime mode, when it is first turned on. This notifies the user that the battery voltage is adequate and the unit is operating properly. If this signal does not occur, the battery needs to be replaced. Obviously, if the signal does not occur when a fresh battery is installed, the unit is malfunctioning and should not be used.

While particular embodiments of the present invention have been illustrated and described herein, it is not intended that these illustrations and descriptions limit the invention. Changes and modifications may be made herein without departing from the scope and spirit of the following claims.

What is claimed is:

1. A device for monitoring the activity of an individual to provide an alarm for detecting anomalous activity by the individual, comprising:

a sensor adapted to simultaneously and continuously measure acceleration in three orthogonal axes and to generate a voltage output that is linearly proportional to the amplitude of detected acceleraton by the individual in each axis;

interface electronics to generate a first reference bias voltage $V_{ref1}$ for each axis of said sensor;

amplifier circuit for defining a user adjustable second reference voltage $V_{ref2}$;

amplifier circuit for amplifying each voltage output, and for continuously comparing each voltage output to said second reference voltage to produce a digital signal defining a single event;

a microcontroller for receiving said digital signal, said microcontroller being programmed to discriminate between normal activity and anomalous activity by identifying a continuous series of events within sequences of preselected time intervals and sending an alarm signal upon detection of said anomalous activity;

an alarm for receiving said alarm signal and signaling an alarm; and the microcontroller conserving power when no events are detected.

2. The device of claim 1, wherein said sensor is a triaxial accelerometer producing said voltage output.

3. The device of claim 1, which further includes JFET buffering circuits for said voltage output.

4. The device of claim 3, which further includes a buffered voltage divider circuit to generate said first reference voltage $V_{ref1}$.

5. The device of claim 1, wherein said amplifier electronics include high pass filters to minimize DC offset.

6. The device of claim 1, which further includes a hex rotary switch for setting the sensitivity of the device.

7. The device of claim 1, which is operable in a daytime mode by including a 3-Volt coin cell lithium battery for its power source and said alarm provides an audible signal.

8. The device of claim 7, wherein said microprocessor operates on the microcode listed in Table II of this specification.

9. The device of claim 1, which is operable in a nighttime mode by including a 12 volt battery for its power source and said alarm provides a radio frequency signal to a remote compatible receiver when alarm criteria are satisfied.

* * * * *